US010886559B2

(12) United States Patent
Azagarsamy et al.

(10) Patent No.: US 10,886,559 B2
(45) Date of Patent: Jan. 5, 2021

(54) POLY(ANHYDRIDE)-BASED POLYMER ELECTROLYTES FOR HIGH VOLTAGE LITHIUM ION BATTERIES

(71) Applicant: Robert Bosch GmbH, Stuttgart (DE)

(72) Inventors: Malar Azagarsamy, Fremont, CA (US); Kulandaivelu Sivanandan, Fremont, CA (US); Hany Basam Eitouni, Oakland, CA (US); Jonathan P. Mailoa, Cambridge, MA (US); Georgy Samsonidze, Boston, MA (US); Karim R. Gadelrab, Boston, MA (US); Boris Kozinsky, Waban, MA (US)

(73) Assignee: Robert Bosch GmbH, Stuttgart (DE)

( * ) Notice: Subject to any disclaimer, the term of this patent is extended or adjusted under 35 U.S.C. 154(b) by 143 days.

(21) Appl. No.: 15/839,754

(22) Filed: Dec. 12, 2017

(65) Prior Publication Data

US 2019/0131653 A1    May 2, 2019

Related U.S. Application Data

(63) Continuation of application No. PCT/US2017/059381, filed on Oct. 31, 2017.

(51) Int. Cl.
*H01M 4/58* (2010.01)
*H01M 10/0525* (2010.01)
(Continued)

(52) U.S. Cl.
CPC ....... *H01M 10/0525* (2013.01); *C07C 317/14* (2013.01); *C07C 317/26* (2013.01);
(Continued)

(58) Field of Classification Search
CPC .... H01M 4/5825; H01M 4/525; H01M 4/505; H01M 4/382; H01M 10/0565; H01M 10/0525; H01M 10/056; H01M 10/052; H01M 10/0566; H01M 10/0585; H01M 2004/028; H01M 2300/0025; H01M 2300/0082; H01M 2300/0091;
(Continued)

(56) References Cited

U.S. PATENT DOCUMENTS

| 8,372,548 B2 | 2/2013 | Lee et al. |
| 2009/0029250 A1 | 1/2009 | Stebani et al. |

(Continued)

FOREIGN PATENT DOCUMENTS

JP    2002-33016    *    1/2002

OTHER PUBLICATIONS

International Search Report for PCT/US17/59381 dated Feb. 22, 2018.
(Continued)

*Primary Examiner* — Laura Weiner
(74) *Attorney, Agent, or Firm* — Brooks Kushman P.C.

(57) ABSTRACT

New poly(anhydride)-based polymers have been synthesized. When these polymers are combined with electrolyte salts, such polymer electrolytes have shown excellent electrochemical oxidation stability in lithium battery cells. Their stability along with their excellent ionic transport properties make them especially suitable as electrolytes in high energy density lithium battery cells.

11 Claims, 5 Drawing Sheets

(51) Int. Cl.
*H01M 10/0565* (2010.01)
*C07C 317/14* (2006.01)
*C08G 69/04* (2006.01)
*C08G 69/12* (2006.01)
*C07C 317/26* (2006.01)
*C08G 61/12* (2006.01)
*H01M 4/36* (2006.01)
*H01M 10/056* (2010.01)
*H01M 10/052* (2010.01)
*H01M 4/505* (2010.01)
*H01M 4/525* (2010.01)
*H01M 4/38* (2006.01)
*H01M 10/0566* (2010.01)
*H01M 10/0585* (2010.01)

(52) U.S. Cl.
CPC .............. *C08G 61/12* (2013.01); *C08G 69/04* (2013.01); *C08G 69/12* (2013.01); *H01M 4/364* (2013.01); *H01M 4/382* (2013.01); *H01M 4/505* (2013.01); *H01M 4/525* (2013.01); *H01M 10/052* (2013.01); *H01M 10/056* (2013.01); *H01M 10/0565* (2013.01); *C08G 2261/334* (2013.01); *C08G 2261/419* (2013.01); *H01M 10/0566* (2013.01); *H01M 10/0585* (2013.01); *H01M 2300/0025* (2013.01); *H01M 2300/0065* (2013.01); *H01M 2300/0082* (2013.01); *H01M 2300/0091* (2013.01); *H01M 2300/0094* (2013.01)

(58) Field of Classification Search
CPC .. H01M 2300/0094; H01M 2300/0065; C08G 61/12
See application file for complete search history.

(56) References Cited

U.S. PATENT DOCUMENTS

2012/0141881 A1* 6/2012 Geier .................... H01M 4/525
429/231.6
2014/0363746 A1 12/2014 He et al.
2014/0370382 A1 12/2014 Lim
2017/0187063 A1 6/2017 Pistorino et al.

OTHER PUBLICATIONS

Lee, "Ionic conductivity in the poly(ethylene malonate) / lithium triflate system," Solid State Ionics 138 (2001) 273-276.

* cited by examiner

POLY(ANHYDRIDE)-BASED POLYMER ELECTROLYTES FOR HIGH VOLTAGE LITHIUM ION BATTERIES

CROSS-REFERENCE TO RELATED APPLICATIONS

This application is a continuation of International Patent Application Number PCTUS2017/059381, filed Oct. 31, 2017, which is incorporated by reference herein.

BACKGROUND OF THE INVENTION

Field of the Invention

This invention relates generally to electrolytes for lithium batteries, and, more specifically, to electrolytes that are especially suited for use in cathodes and at high voltages.

More and more lithium battery manufacturers are using next-generation cathode materials such as NCA (lithium nickel cobalt aluminum oxide), NCM (lithium nickel cobalt manganese oxide), and high energy NCM (HE-NCM-magnesium-rich lithium nickel cobalt manganese oxide) in order to exploit their potentially high gravimetric energy densities (as high as 300-500 Wh/kg), their good rate capabilities, and their long-term stability. Cells made with such oxidic cathode materials often operate at higher voltages (e.g., as high as 4.7V) than do cells (e.g., 3.6-3.8V) with olivine cathode materials such as LFP (lithium iron phosphate). Electrolytes that have been stable at the lower voltages of LFP cells may have difficulty operating at the higher voltages, especially in the cathode. Degradation, in the form of oxidation, may lead to capacity fade early in the life of a cell.

Thus, there is a need to develop electrolytes that are especially well-suited to operate in the high voltage conditions of next generation cathode materials.

SUMMARY

In one embodiment of the invention, a polymer is described. The polymer includes an anhydride-based polymer structure described by:

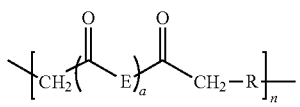

wherein E is selected from the group consisting of nitrogen (N) with a substituent Z, oxygen (O), and sulfur (S); a is an integer that ranges from 1 to 5; n is an integer that ranges from 1 to 1000;

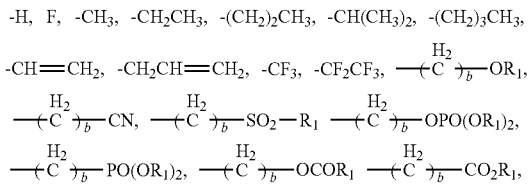

each Z is selected independently from the group consisting of:
wherein each $R_1$ is selected independently from the group consisting of hydrogen, methyl, ethyl, propyl, and isopropyl groups; and b is an integer that ranges from 1 to 10; each R is selected independently from the group consisting of:

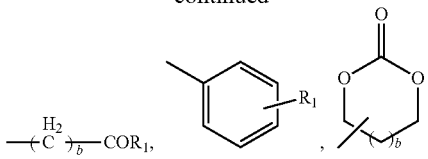

wherein each X is selected independently from the group consisting of hydrogen, fluorine, methyl, ethyl, isopropyl, and trifluoromethyl groups; and c, d, and e are integers, and each ranges independently from 0 to 10.

In one arrangement, the anhydride-based polymer structure is described by:

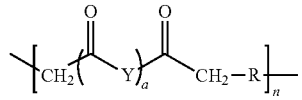

wherein Y is either oxygen (O) or sulfur (S).

In another arrangement, the anhydride-based polymer structure is described by:

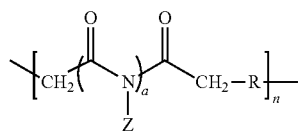

In some embodiments of the invention, any of the polymers described herein are combined with an electrolyte salt to become polymer electrolytes.

In one embodiment of the invention any of the polymer electrolytes described herein further include ceramic electrolyte particles.

In some arrangements, any of the polymers described herein are crosslinked and may or may not be combined with an electrolyte salt to become polymer electrolytes.

In one embodiment of the invention, a positive electrode includes a positive electrode active material; and a catholyte comprising any of the electrolytes described herein. The positive electrode active material particles and the catholyte are mixed together. The catholyte may also include a solid polymer electrolyte. The catholyte may also include ceramic electrolyte particles. The catholyte may be crosslinked. The catholyte may contain an electrolyte salt that is a lithium salt.

The positive electrode active material may be any of lithium iron phosphate, lithium metal phosphate, divanadium pentoxide, lithium nickel cobalt aluminum oxide, lithium nickel cobalt manganese oxide, magnesium-rich lithium nickel cobalt manganese oxide, lithium manganese spinel, lithium nickel manganese spinel, and combinations thereof.

In another embodiment of the invention an electrochemical cell includes an anode configured to absorb and release lithium ions; a cathode comprising cathode active material particles, an electronically-conductive additive, and a first catholyte; a current collector adjacent to an outside surface of the cathode; and a separator region between the anode and the cathode, the separator region comprising a separator electrolyte configured to facilitate movement of lithium ions back and forth between the anode and the cathode. The first catholyte may include any of the electrolytes described herein. The first catholyte may also contain ceramic electrolyte particles. The first catholyte may be crosslinked The electrolyte salt may be a lithium salt.

The first catholyte and/or the separator electrolyte may also contain a solid polymer electrolyte. In one arrangement, the first catholyte and the separator electrolyte are the same.

In one arrangement, there is an overlayer between the cathode and the separator region. The overlayer includes a second catholyte, which may be any of the electrolytes disclosed herein. The first catholyte and the second catholyte may or may not be the same.

The anode may contain any of lithium metal, lithium alloy, lithium titanate, graphite and silicon.

BRIEF DESCRIPTION OF THE DRAWINGS

The foregoing aspects and others will be readily appreciated by the skilled artisan from the following description of illustrative embodiments when read in conjunction with the accompanying drawings.

DETAILED DESCRIPTION

Figure 1:
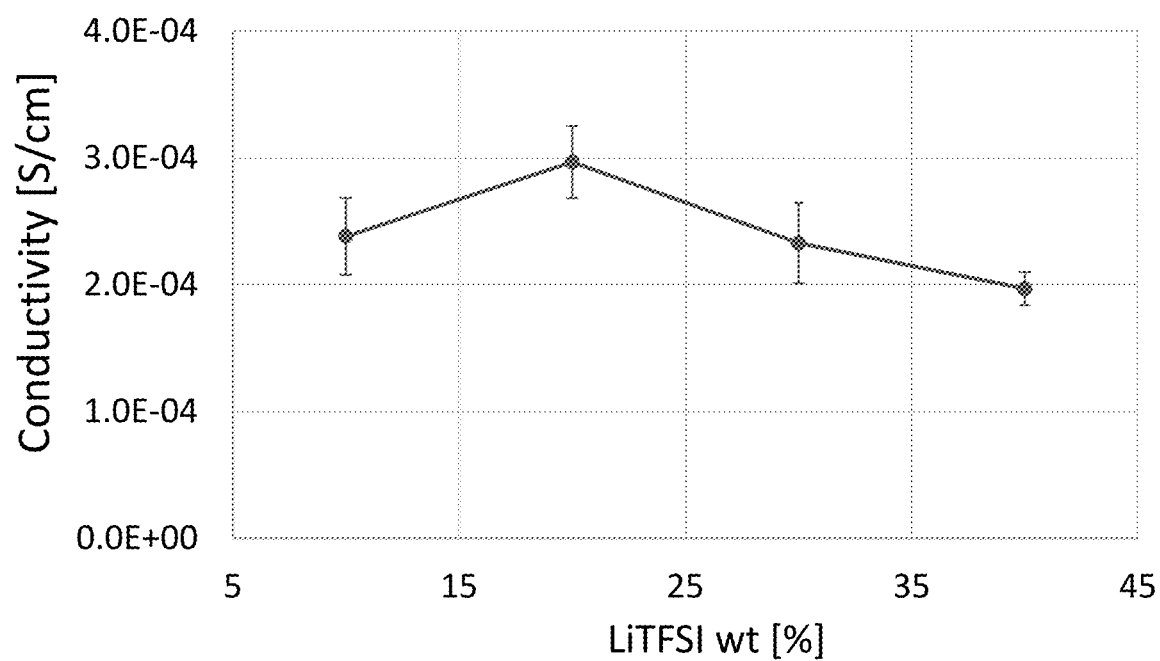
FIG. 1 is a graph that shows ionic conductivities of poly(butenoic anhydride) electrolytes with various concentrations of LiTFSI at 80° C., according to an embodiment of the invention.

The embodiments of the invention are illustrated in the context of anhydride polymers that can be used as electrolytes or electrolyte additives in lithium battery cells and the like. The skilled artisan will readily appreciate, however, that the materials and methods disclosed herein will have application in a number of other contexts where high-voltage electrolytes are desirable, particularly where long-term stability is important.

These and other objects and advantages of the present invention will become more fully apparent from the following description taken in conjunction with the accompanying drawings.

All publications referred to herein are incorporated by reference in their entirety for all purposes as if fully set forth herein.

In this disclosure, the terms "negative electrode" and "anode" are both used to describe a negative electrode. Likewise, the terms "positive electrode" and "cathode" are both used to describe a positive electrode.

It is to be understood that the terms "lithium metal" or "lithium foil," as used herein with respect to negative electrodes, describe both pure lithium metal and lithium-rich metal alloys as are known in the art. Examples of lithium rich metal alloys suitable for use as anodes include Li—Al, Li—Si, Li—Sn, Li—Hg, Li—Zn, Li—Pb, Li—C or any other Li-metal alloy suitable for use in lithium metal batteries. Other negative electrode materials that can be used in the embodiments of the invention include materials in which lithium can intercalate, such as graphite, and other materials that can absorb and release lithium ions, such as silicon, germanium, tin, and alloys thereof. Many embodiments described herein are directed to batteries with solid polymer electrolytes, which serve the functions of both electrolyte and separator. As it is well known in the art, batteries with liquid electrolytes use an inactive separator material that is distinct from the liquid electrolyte.

The following construction is used throughout this disclosure: "each variable is chosen independently" from a list that is provided. An example of this usage can be found with reference to X groups in some of the inventive polymer structures in which there are many X's. The example is, "each X may be chosen independently from hydrogen, fluorine, methyl, ethyl, isopropyl, and trifluoromethyl groups." This construction is used to mean that for a particular X in the structure, any of the groups in the list may be used. In choosing a group to use for another X in the structure, any of the groups in the list may be used with no regard to the choices that have been made for other X groups. Thus, the following arrangements are all possible: all the X's may be the same, all the X's may be different, or some X's may be the same and some may be different.

The molecular weights given herein are number-averaged molecular weights.

In this disclosure, ranges of values are given for many variables. It should be understood that the possible values for any variable also include any range subsumed within the given range.

Based on repeated observation of $Li^+$ interaction with other atoms in molecular dynamics (MD) simulations, it seems that $Li^+$ coordinates with partially-negatively-charged atoms in a polymer electrolyte or, when the Li-salt is not soluble in the polymer, with negatively charged anions of the salt that has been added to a polymer to form the electrolyte. With polyethylene oxide (PEO), $Li^+$ coordinates with partially-negatively-charged oxygen atoms in the PEO. Similarly, in poly(anhydride)s, $Li^+$ coordinates with partially-negatively charged oxygens in the carbonyl groups.

Poly(anhydride)s exhibit high oxidative stability. One reason for this is the stability of the keto isomer of the anhydride. Other carbonyl-containing molecular structures, such as ketones, may undergo isomerization to form an enol tautomer. Yet in anhydrides, the lack of an acidic methylene or proton group prevents such tautomerization. For example, a poly(anhydride) with 3 oxygen atoms per repeat unit as shown below cannot form an enol isomer via an active methylene group route as there is no strongly acidic methylene group in the structure. A proton transfer from an inactive methylene group will result in a high energy enol structure, which is not likely to form and would quickly revert back to the stable keto form, as shown below.

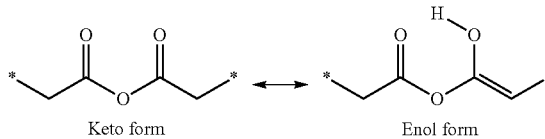

Keto form  Enol form

Poly(anhydride), Poly(thioanhydride), and Poly(imide):

In some embodiments of the invention, two general structures for poly(anhydride)-based polymers are shown below. Structure A shows the general structure for poly (anhydride) when Y is oxygen (O) and for poly(thioanhydride) when Y is sulfur (S). Structure B is an imide-based polymer with nitrogen atom (N) in place of the oxygen or sulfur atoms shown in structure A. Structure B has functional side chains Z that can be attached either directly as shown or through extendable alkyl chains (not shown).

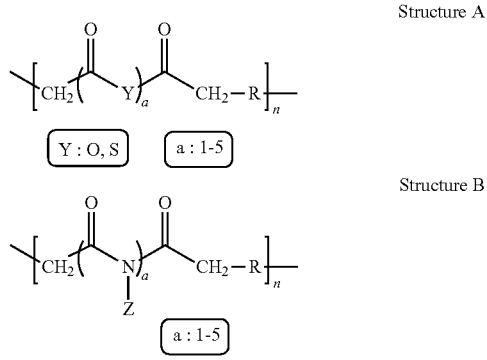

Each Z and R is chosen independently from the lists below, a is an integer that ranges from 1 to 5, and n is an integer that ranges from 1 to 1000.

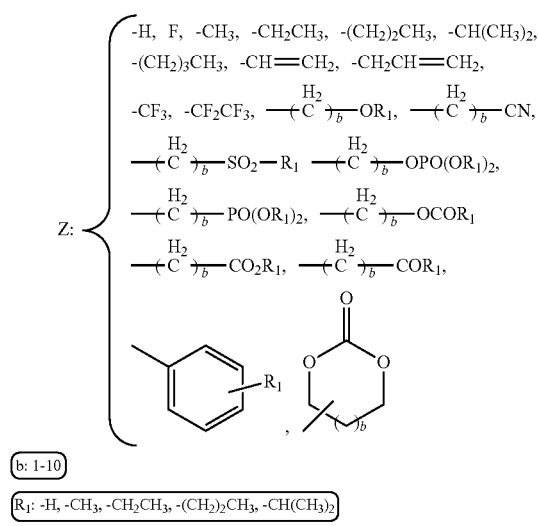

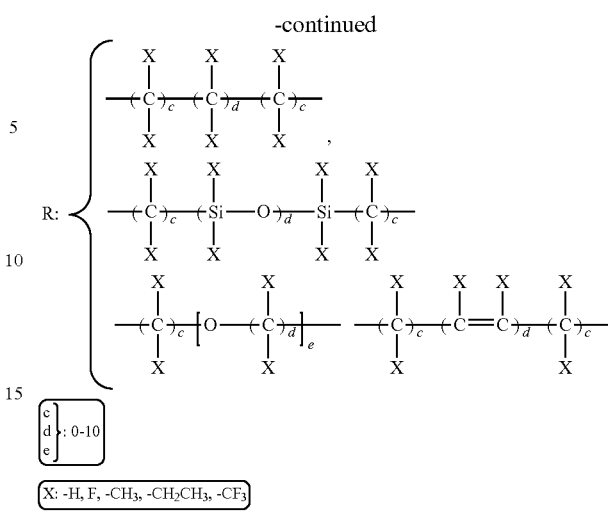

In the Z groups, b is an integer that ranges from 1 to 10, and each $R_1$ may be chosen independently from hydrogen, methyl, ethyl, propyl, or isopropyl groups. In the R groups; c, d, and e are integers, and each ranges independently from 1 to 10; and each X may be chosen independently from hydrogen, fluorine, methyl, ethyl, isopropyl, and trifluoromethyl groups.

In another embodiment of the invention, Structure A and Structure B include crosslinkable Z groups and/or R groups, which make it possible for such poly(anhydride)-based polymers to be crosslinked. Examples of such crosslinkable Z groups include, but are not limited to, vinyl and allyl groups. Examples of such crosslinkable R groups include, but are not limited to, unsaturated polyolefins such as polybutadiene and polyisoprene. When Structure A or Structure B includes one or more such crosslinkable group(s), it is possible to crosslink the structures using a number of approaches including thermal or UV generation of radicals, click chemistries, hydrosilylation, transesterification, or any other commonly used crosslinking strategy.

Alternatively, Structure A and Structure B may be shown combined as one condensed Structure C as follows:

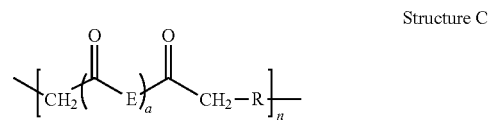

Structure C wherein E may be, as for Structure A, O, or S, or as for Structure B, N with a substituent Z. All other values are as described above in reference to Structures A and B.

In another embodiment of the invention, particles of ceramic electrolyte are mixed into a poly(anhydride)-based polymer electrolyte to form an enhanced composite electrolyte with superior ionic transport and mechanical properties. Such a composite electrolyte may be used in a lithium battery cell in the separator region or in the cathode. Examples of ceramic electrolytes that are useful for mixing with poly(anhydride)-based polymer electrolytes include, but are not limited to, those shown in Table 1 below.

TABLE 1

Exemplary Ceramic Conductors for Use as Additives in
Poly(anhydride)-Based Polymer Electrolytes

| Electrolyte Type | Exemplary Formulas | Mixture Proportion |
|---|---|---|
| Oxynitride glass | $Li_xPO_yN_z$ $x = 2.9$, $y = 3.3$, $z = 0.46$ $0.24 < z < 1.2$ | |
| | $Li_xBO_yN_z$ | |
| Sulfide and oxysulfide glass | $Li_2S \bullet P_2S_5$ | 0.75:0.25 |
| | $Li_2S \bullet SiS_2$ | 0.6:0.4 |
| | $Li_2S \bullet SiS_2 \bullet Li_xMO_4$ M = Si, P, Ge | 0.57:0.38:0.05 |
| | $Li_2S \bullet SiS_2 \bullet Li_3PO_4$ | 0.63:0.36:0.01 |
| | $Li_2S \bullet SiS_2 \bullet xMS_y$ M = Sn, Ta, Ti | 0.6:0.4:0.01-0.05 |
| | $Li_2S \bullet SiS_2 \bullet Li_3N$ | 0.55:0.40:0.03 |
| Li thionitride glass | $Li_3N \bullet SiS_2$ | 0.4:0.6 |
| LLTO Perovskite structure (Ohara type) | $La_{2/3-x}Li_{3x}TiO_3$ $0.03 \leq x \leq 0.167$ | |
| | $La_{1/3-x}Li_{3x}TaO_3$ $0.025 \leq x \leq 0.167$ | |
| | $La_{1/3-x}Li_{3x}NbO_3$ $0 \leq x \leq 0.06$ | |
| Nasicon-type (Lisicon) phosphate | $Li_{1.3}Ti_{1.7}Al_{0.3}(PO_4)_3$ | |
| | $LiAlTa(PO_4)_3$ | |
| | $LiAl_{0.4}Ge_{1.6}(PO_4)_3$ | |
| | $Li_{1.4}Ti_{1.6}Y_{0.4}(PO_4)_3$ | |
| | $Li_{3-2x}(Sc_{1-x}M_x)_2(PO_4)_3$ M = Zr, Ti, $x = 0.1, 0.2$ | |
| | $Li_3Sc_{1.5}Fe_{0.5}(PO_4)_3$ | |

*denotes that components are mixed together

Table 2 below shows lithium ion transport properties for polyethylene oxide (PEO), and various poly(anhydride)-based polymers based on MD simulation. It is clear that poly(heptanoic anhydride) has a higher conductivity than some of the other structures. Examples of other variations of poly(anhydride)-based polymers include, but are not limited to, poly(thioanhydride) and poly(imide), which are shown in the table below. These variations are obtained by substituting nitrogen and sulfur atoms for oxygen in anhydride repeat units. Other structural variations include, but are not limited to, substituting one or all oxygen atoms with nitrogen and/or sulfur, changing the alkyl chain length, and changing the alkyl groups on the nitrogen atoms of the imides.

TABLE 2

Lithium Transport Properties of PEO, PPM, and Poly(anhydride)-Based Polymers

| Polymer | Chemical Structure | LiTFSI Concentration (wt %) | κ (S/cm) | $t_+$ |
|---|---|---|---|---|
| Polyethylene oxide | 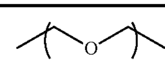 | 30 | $8.2 \pm 2.2 \times 10^{-4}$ | $0.18 \pm 0.07$ |
| Poly(pentylmalonate) | 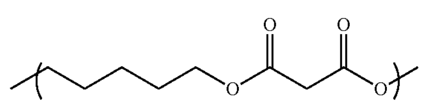 | 30 | $4.4 \times 10^{-4}$ | 0.66 |
| Poly(heptanoicanhydride) | 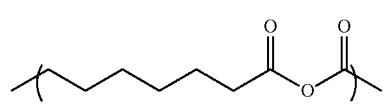 | 30 | $9.7 \times 10^{-4}$ | 0.67 |
| Poly(heptimide) | 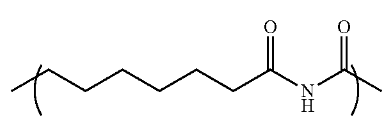 | 30 | $8.2 \times 10^{-6}$ | 0.09 |
| Poly(N-methylheptimide) | 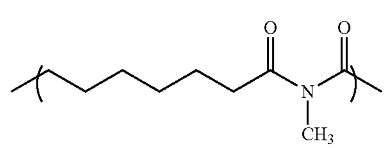 | 30 | — | — |
| Poly(thioheptanoicanhydride) | 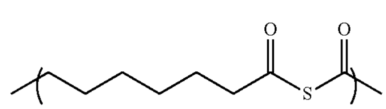 | 30 | $3.5 \times 10^{-5}$ | 0.36 |

TABLE 2-continued

Lithium Transport Properties of PEO, PPM, and Poly(anhydride)-Based Polymers

| Polymer | Chemical Structure | LiTFSI Concentration (wt %) | κ (S/cm) | $t_+$ |
|---|---|---|---|---|
| Poly(2,4-dioxo-1,3,5-triketononane) | 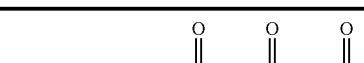 | 30 | $5.2 \times 10^{-4}$ | 0.77 |
| Poly(2,4-diamino-1,3,5-triketononane) | 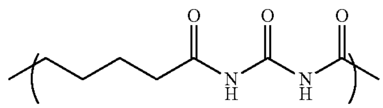 | — | — | — |
| Poly(2,4-dithio-1,3,5-triketononane) | 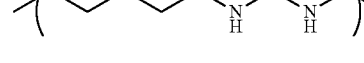 | — | — | — |
| Poly(cis-hept-4-enoicanhydride) | 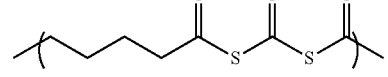 | 30 | $1.26 \times 10^{-3}$ | 0.79 |

Anhydride Group Chemical Stability

Table 3 shows ionization potentials (IP) and the energy difference between tautomers of anhydride groups as simulated using quantum chemistry (QC) (method: M06-HF/aug-cc-pvtz//PBEO/aug-cc-pvtz). The enol-form of an anhydride group is difficult to form as shown by the 0.66 eV energy required to convert the keto- to the enol-form; however, if formed, it is easier to oxidize the enol-form (lower IP) than it is to oxidize the keto-form. Due to the high energy required to form the enol-form, as well as the relatively high IP of both the keto- and enol-forms, QC predicts that the anhydride group is quite stable against oxidation.

TABLE 3

Ionization potentials (IP) and energy difference between tautomers of anhydride groups

| Group | Keto-form | Enol-form | $E_{Enol}-E_{Keto}$ |
|---|---|---|---|
| Anhydride | 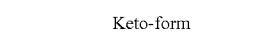<br>IP = 11.06 eV | <br>IP = 8.88 eV | 0.66 eV |

Anhydride Conductivity

Symmetric cells were built by sandwiching various poly(butenoic anhydride) electrolytes between two aluminum electrodes. The poly(butenoic anhydride) electrolytes had different LiTFSI lithium salt concentrations. The ionic conductivities of the electrolytes were measured at 80° C. using impedance spectroscopy and are shown in the graph of ionic conductivity as a function of salt concentration in FIG. 1. The data clearly show that poly(butenoic anhydride) electrolytes have substantial lithium ion conductivities at 80° C.

Anhydride Group Electrochemical Stability

Figure 2:
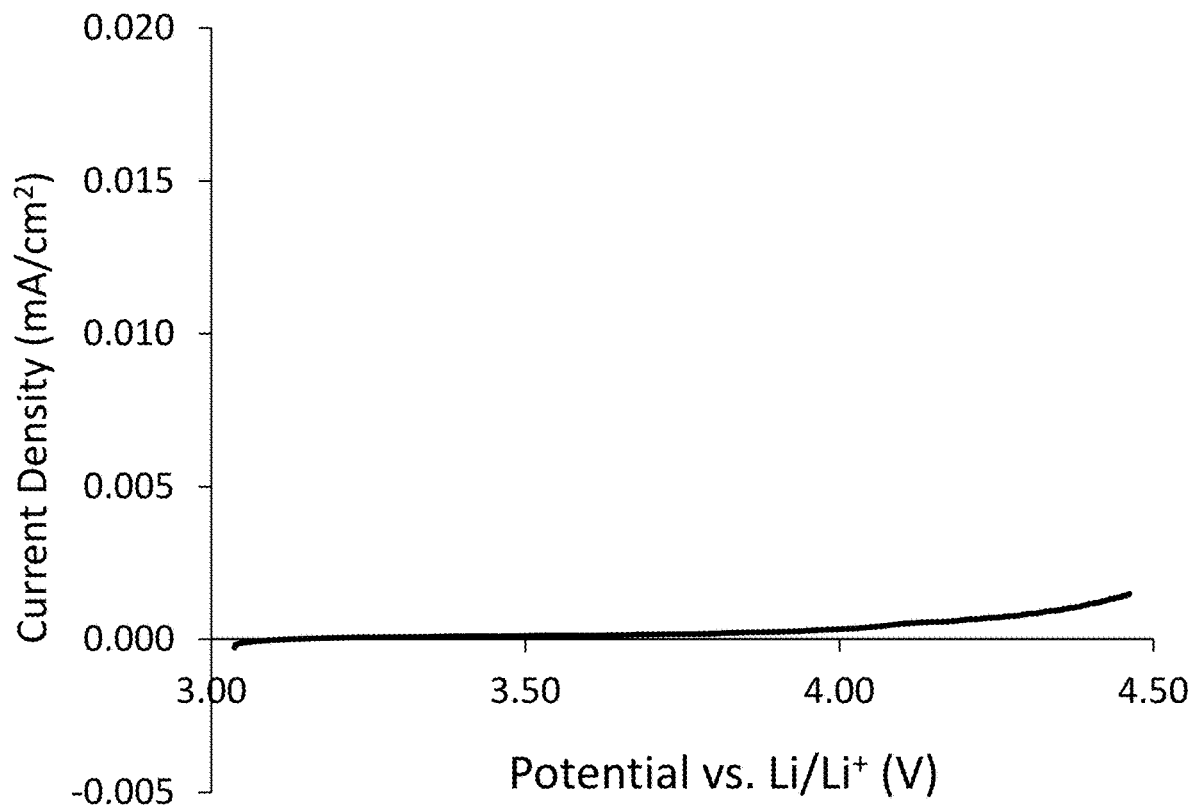
FIG. 2 is a graph that shows cyclic voltammetry data for 0.1M of 4-pentenoic anhydride and 0.1M of $LiBF_4$ in propylene carbonate, according to an embodiment of the invention.

Cyclic voltammetry was measured using a three-electrode system that included a Pt button working electrode, a Pt wire counter electrode, and a quasi-reference electrode constructed from an Ag wire dipped in a 10 mM $AgNO_3$ in 0.1 M tetrabutylammonium hexafluorophosphate solution in glass tubing with an attached Vycor frit. The quasi-reference electrode was first calibrated against a 10 mM ferrocene solution in 0.1 M lithium tetrafluoroborate ($LiBF_4$) in propylene carbonate, to give $E_{ox}$ (ferrocene/ferrocenium) =0.058 V (vs. $Ag/Ag^+$). Then the same ferrocene solution was used to calibrate a lithium reference electrode ($E_{ox}$ (ferrocene/ferrocenium)=3.35-3.39 V (vs. $Li/Li^+$)). The cyclic voltammetry was carried out on 0.1M solution of 4-pentenoic anhydride in 0.1M $LiBF_4$ in propylene carbonate and at a scan rate of 5 mV/s. The cyclic voltammetry data were then standardized for $Li/Li^+$ to reflect oxidation stability in a lithium cell, as electrolyte materials made from 4-pentenoic anhydride can interact with electrodes in an actual battery cell. The results are shown in the graph in FIG. 2. As shown in FIG. 2, 4-pentenoic anhydride had electrochemical oxidation stability up to at least 4.5 V with insignificant current density response even at 4.5 V. This clearly indicates that this type of anhydride-based system is stable at high voltages and can be used as an electrolyte in high energy density lithium ion batteries.

Cell Designs that Include Anhydride-Based Polymers

Figure 3:
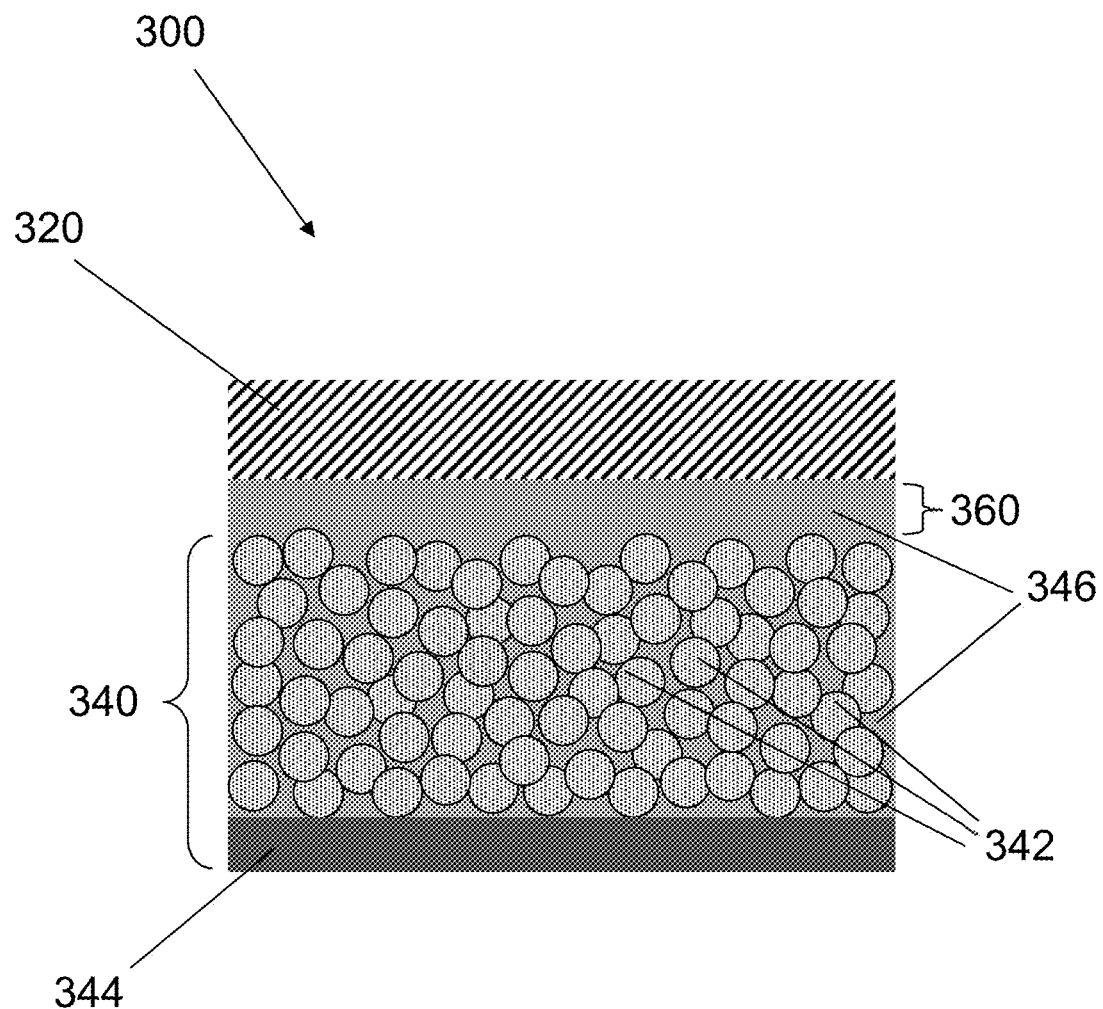
FIG. 3 is a schematic illustration of one configuration of a lithium battery cell that contains an electrolyte that is used in both the cathode and the separator, according to an embodiment of the invention.

In one embodiment of the invention, a lithium battery cell 300 has an anode 320 that is configured to absorb and release lithium ions, as shown in FIG. 3. The anode 320 may be a lithium or lithium alloy foil or it may be made of a material into which lithium ions can be absorbed such as graphite or silicon. Other choices for the anode 320 include, but are not limited to, lithium titanate, and lithium-silicon alloys. The lithium battery cell 300 also has a cathode 340 that includes cathode active material particles 342, an electronically-conductive additive such as carbon black (not shown), a current collector 344, a catholyte (electrolyte in the cathode) 346, and an optional binder (not shown). In one arrangement, the catholyte 346 includes any of the anhydride-based polymer electrolytes disclosed above. In another arrangement, the catholyte 346 includes mixtures or combinations of other solid polymer electrolytes with anhydride-based polymer electrolytes. There is a separator region 360 between the anode 320 and the cathode 340. The catholyte 346 extends all the way into the separator region 360 and facilitates movement of lithium ions back and forth between the anode 320 and the cathode 340 as the cell 300 cycles. The electrolyte 346 in the separator region 360 and the catholyte 346 in the cathode 340 are the same.

Figure 4:
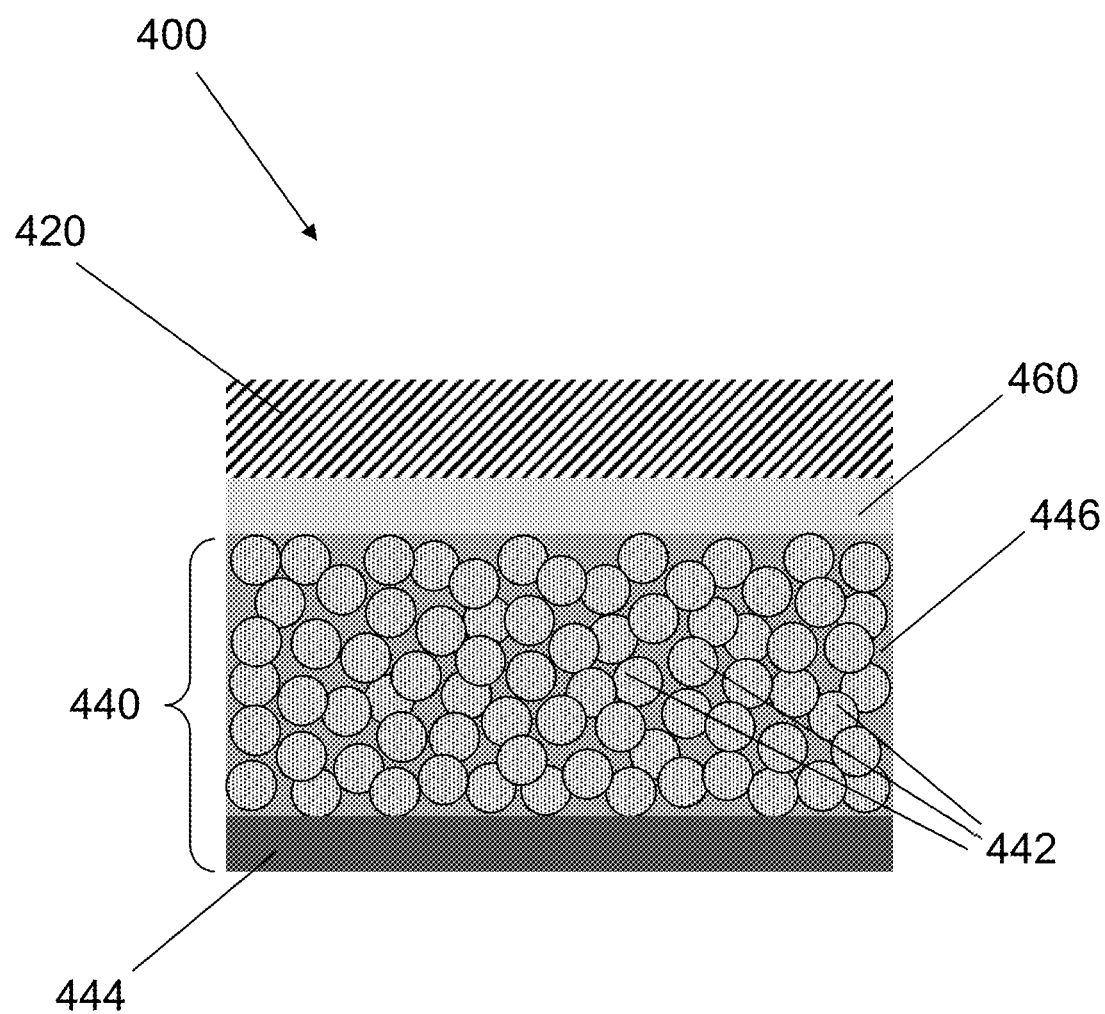
FIG. 4 is a schematic illustration of another configuration of a lithium battery cell that contains a catholyte and a separator electrolyte different from the catholyte, according to an embodiment of the invention.

In another embodiment of the invention, a lithium battery cell 400 has an anode 420 that is configured to absorb and release lithium ions as shown in FIG. 4. The anode 420 may be a lithium or lithium alloy foil or it may be made of a material into which lithium ions can be absorbed such as graphite or silicon. Other choices for the anode 420 include, but are not limited to, lithium titanate, and lithium-silicon alloys. The lithium battery cell 400 also has a cathode 440 that includes cathode active material particles 442, an electronically-conductive additive such as carbon black (not shown), a current collector 444, a catholyte 446, and an optional binder (not shown). In one arrangement, the catholyte 446 includes any of the anhydride-based polymer electrolytes disclosed above. In another arrangement, the catholyte 446 includes mixtures or combinations of other solid polymer electrolytes with anhydride-based polymer electrolytes. There is a separator electrolyte 460 between the anode 420 and the cathode 440. The separator electrolyte 460 facilitates movement of lithium ions back and forth between the anode 420 and the cathode 440 as the cell 400 cycles. The separator electrolyte 460 may include any electrolyte that is suitable for use in a lithium battery cell. In one arrangement, the separator electrolyte 460 contains a liquid electrolyte that is soaked into a porous plastic material (not shown). In another arrangement, the separator electrolyte 460 contains a viscous liquid or gel electrolyte. In another arrangement, the separator region 460 contains a solid polymer electrolyte in which the anhydride-based polymer is immiscible.

Figure 5:
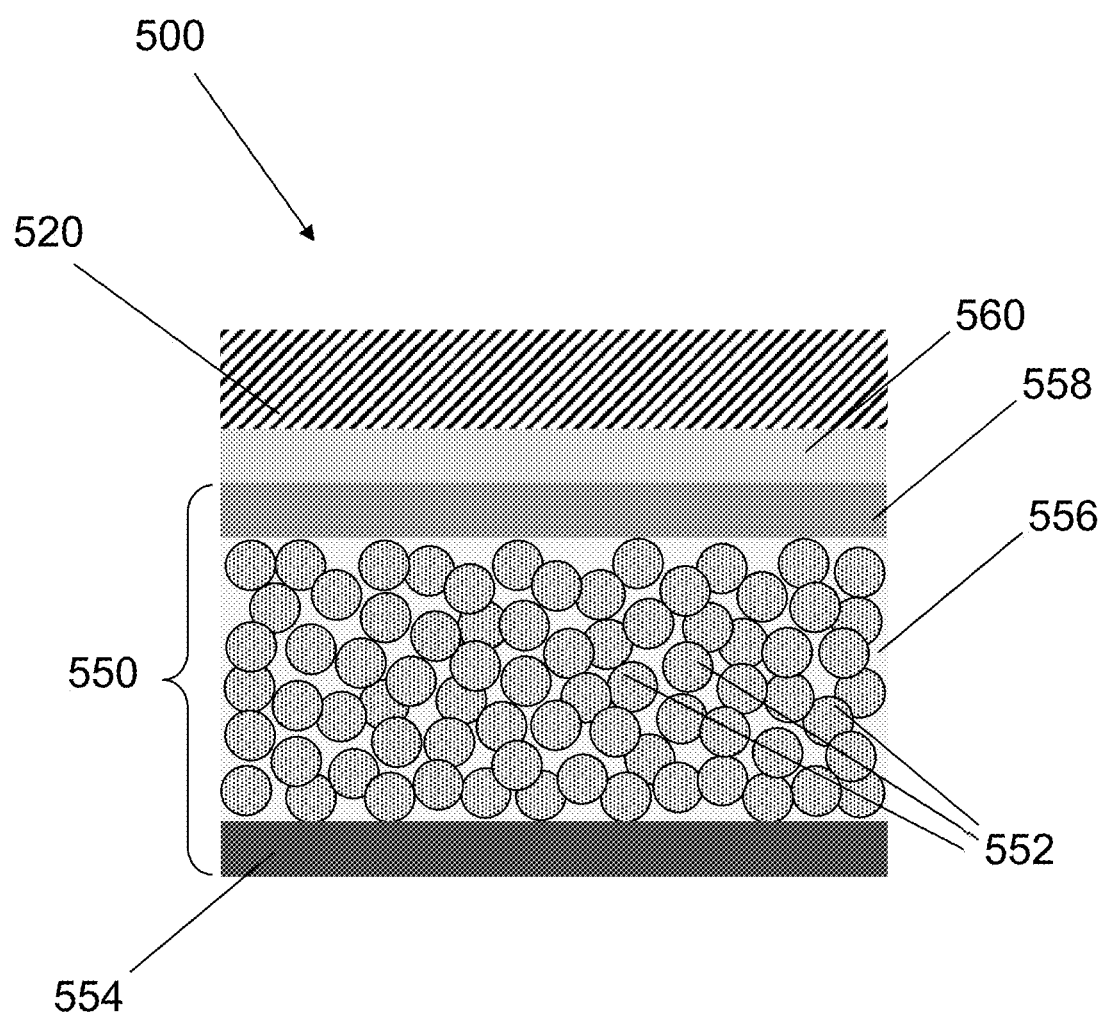
FIG. 5 is a schematic illustration of another configuration of a lithium battery cell that contains a catholyte and a cathode overlayer, according to an embodiment of the invention.

In another embodiment of the invention, a battery cell with a third configuration is described. With reference to FIG. 5, a lithium battery cell 500 has an anode 520 that is configured to absorb and release lithium ions. The anode 520 may be a lithium or lithium alloy foil or it may be made of a material into which lithium ions can be absorbed such as graphite or silicon. Other choices for the anode 520 include, but are not limited to, lithium titanate, and lithium-silicon alloys. The lithium battery cell 500 also has a cathode 550 that includes cathode active material particles 552, an electronically-conductive additive (not shown), a current collector 554, a catholyte 556, an optional binder (not shown), and an overcoat layer 558. In one arrangement, the electrolyte in the overcoat layer 558 and the catholyte 556 are the same. In another arrangement, the electrolyte in the overcoat layer 558 and the catholyte 556 are different. The overcoat layer 558 and/or the catholyte 556 may contain any of the anhydride-based polymer electrolytes or mixtures or combinations of other solid polymer electrolytes with anhydride-based polymer electrolytes or electrolyte additives (in a solid polymer electrolyte host) disclosed herein. In one arrangement, the overcoat layer 558 is a solid electrolyte layer. There is a separator region 560 between the anode 520 and the cathode 550. The separator region 560 contains an electrolyte that facilitates movement of lithium ions back and forth between the anode 520 and the cathode 550 as the cell 500 cycles. The separator region may include any electrolyte that is suitable for such use in a lithium battery cell. In one arrangement, the separator electrolyte 560 contains a liquid electrolyte that is soaked into a porous plastic material (not shown). In another arrangement, the separator electrolyte 560 contains a viscous liquid or gel electrolyte. In another arrangement, the separator region 560 contains a solid polymer electrolyte in which the anhydride-based polymer is immiscible.

A solid polymer electrolyte for use in separator region, such as separator regions 460 or 560, can be any electrolyte that is appropriate for use in a Li battery. Of course, many such electrolytes also include electrolyte salt(s) that help to provide ionic conductivity. Examples of such electrolytes include, but are not limited to, block copolymers that contain ionically-conductive blocks and structural blocks that make up ionically-conductive phases and structural phases, respectively. The ionically-conductive phase may contain one or more linear polymers such as polyethers, polyamines, polyimides, polyamides, poly alkyl carbonates, polynitriles, perfluoro polyethers, fluorocarbon polymers substituted with high dielectric constant groups such as nitriles, carbonates, and sulfones, and combinations thereof. In one arrangement, the ionically-conductive phase contains one or more anhydride-based polymer, as disclosed herein. The linear polymers can also be used in combination as graft copolymers with polysiloxanes, polyalkoxysiloxanes, polyphosphazines, polyolefins, and/or polydienes to form the conductive phase. The structural phase can be made of polymers such as polystyrene, hydrogenated polystyrene, polymethacrylate, poly(methyl methacrylate), polyvinylpyridine, polyvinylcyclohexane, polyimide, polyamide, polypropylene, polyolefins, poly(t-butyl vinyl ether), poly(cyclohexyl methacrylate), poly(cyclohexyl vinyl ether), poly(t-butyl vinyl ether), polyethylene, poly(phenylene oxide), poly(2,6-dimethyl-1,4-phenylene oxide), poly(phenylene sulfide), poly(phenylene sulfide sulfone), poly(phenylene sulfide ketone), poly(phenylene sulfide amide), polysulfone, fluorocarbons, such as polyvinylidene fluoride, or copolymers that contain styrene, methacrylate, or vinylpyridine. It is especially useful if the structural phase is rigid and is in a glassy or crystalline state.

With respect to the embodiments described in FIGS. 3, 4, and 5, suitable cathode active materials include, but are not limited to, LFP (lithium iron phosphate), LMP (lithium metal phosphate in which the metal can be Mn, Co, or Ni), $V_2O_5$ (divanadium pentoxide), NCA (lithium nickel cobalt aluminum oxide), NCM (lithium nickel cobalt manganese oxide), high energy NCM (HE-NCM—magnesium-rich lithium nickel cobalt manganese oxide), lithium manganese spinel, lithium nickel manganese spinel, and combinations thereof. Suitable electronically-conductive additives include, but are not limited to, carbon black, graphite, vapor-grown carbon fiber, graphene, carbon nanotubes, and combinations thereof. A binder can be used to hold together the cathode active material particles and the electronically conductive additive. Suitable binders include, but are not limited to, PVDF (polyvinylidene difluoride), PVDF-HFP poly (vinylidene fluoride-co-hexafluoropropylene), PAN (polyacrylonitrile), PAA (polyacrylic acid), PEO (polyethylene oxide), CMC (carboxymethyl cellulose), and SBR (styrene-butadiene rubber).

Examples

The following examples provide details relating to composition, fabrication and performance characteristics of polymer electrolytes in accordance with the present invention. It should be understood the following is representative only, and that the invention is not limited by the detail set forth in these examples.

In one example, a synthetic route using acyclic diene metathesis (ADMET) to produce poly(anhydride)s, specifically poly(butenoic anhydride), is depicted below. Hoveyda-Grubb's second-generation catalyst (0.06 g, 0.1 mmol) was added to a sample of 4-pentenoic anhydride (4 g, 22 mmol) and subjected to high vacuum (1 torr approx.). Bubbling of the reaction mixture was seen due to evolution of ethylene gas. The solution was slowly heated to 60° C. and stirred under high vacuum for 16 hours. After that, the reactor was back-filled with argon, and the polymerization was quenched using a solution of ethyl vinyl ether (0.78 g, 10.8 mmol) in toluene (5 mL) and stirred for half an hour. Slow addition of the polymer solution to petroleum ether (500 mL) afforded poly(butenoic anhydride) as an amber-colored waxy solid, which was dried under high vacuum to obtain 2.6 g of dry polymer in 90% yield. Mn (GPC)=80,000 g/mol.

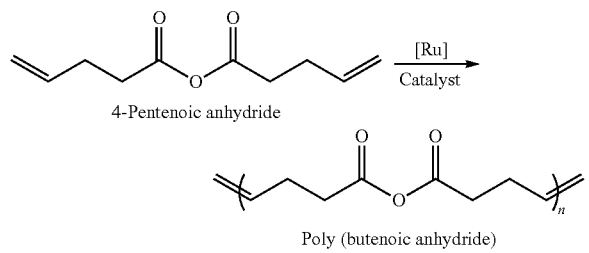

This invention has been described herein in considerable detail to provide those skilled in the art with information relevant to apply the novel principles and to construct and use such specialized components as are required. However, it is to be understood that the invention can be carried out by different equipment, materials and devices, and that various modifications, both as to the equipment and operating procedures, can be accomplished without departing from the scope of the invention itself.

We claim:
1. A positive electrode comprising:
a positive electrode active material comprising lithium iron phosphate; and
a catholyte comprising an anhydride-based polymer electrolyte having a structure described by:

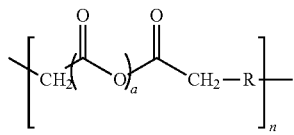

wherein a is an integer that ranges from 1 to 5, n is an integer from 1 to 1,000, R is

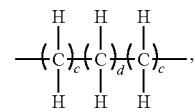

c is 0 to 10, and d is 0 to 10, wherein c or d is greater than 0; and
wherein the positive electrode active material and the catholyte are mixed together, and the catholyte further comprises glass ceramic electrolyte particles mixed with the anhydride-based polymer electrolyte.

2. The positive electrode of claim 1 wherein the catholyte further comprises a solid polymer electrolyte.

3. The positive electrode of claim 1 wherein the catholyte is crosslinked.

4. The positive electrode of claim 1 wherein the catholyte further comprises an electrolyte salt comprising a lithium salt.

5. The positive electrode of claim 1, wherein the glass ceramic electrolyte particles are selected from the group consisting of oxynitride glass, sulfide glass, oxysulfide glass, lithium thionitride glass, lithium lanthanum titanate perovskite glass material, lisicon phosphate-based glass material, and combinations thereof.

6. An electrochemical cell, comprising:
an anode configured to absorb and release lithium ions the anode comprises a lithium metal material;
a cathode comprising cathode active material particles, an electronically-conductive additive of carbon black, and a catholyte;
a current collector adjacent to an outside surface of the cathode; and
a separator region between the anode and the cathode, the separator region comprising a solid polymer electrolyte configured to facilitate movement of lithium ions back and forth between the anode and the cathode;
wherein the catholyte comprises an anhydride-based polymer structure described by:

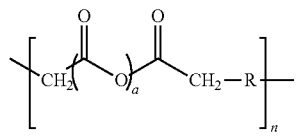

wherein a is an integer that ranges from 1 to 5, n is an integer from 1 to 1,000, R is

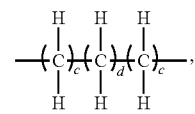

c is 0 to 10, and d is 0 to 10, is wherein c or d is greater than 0;
and the electrolyte salt is a lithium salt, and the catholyte further comprises glass ceramic electrolyte particles mixed with the anhydride-based polymer electrolyte.

7. The electrochemical cell of claim 6 wherein the catholyte further comprises a solid polymer electrolyte.

8. The electrochemical cell of claim 6 wherein the catholyte and the separator electrolyte are the same material.

9. The electrochemical cell of claim 6 further comprising an overlayer between the cathode and the separator region.

10. The electrochemical cell of claim 6 wherein the catholyte is crosslinked.

11. The positive electrolyte of claim 6, wherein the glass ceramic electrolyte particles are selected from the group consisting of oxynitride glass, sulfide glass, oxysulfide glass, lithium thionitride glass, lithium lanthanum titanate perovskite glass material, lisicon phosphate-based glass material, and combinations thereof.

* * * * *